US006306120B1

(12) United States Patent
Tan

(10) Patent No.: US 6,306,120 B1
(45) Date of Patent: Oct. 23, 2001

(54) APPLICATOR AND METHOD FOR DELIVERY OF MITOMYCIN TO EYE TISSUES DURING GLAUCOMA FILTERING SURGERY

(76) Inventor: Ben Gee Tan, 20924 Kelly Rd., Eastpointe, MI (US) 48021

( * ) Notice: Subject to any disclaimer, the term of this patent is extended or adjusted under 35 U.S.C. 154(b) by 0 days.

(21) Appl. No.: 09/327,098

(22) Filed: Jun. 7, 1999

(51) Int. Cl.[7] .................................................. A61M 35/00
(52) U.S. Cl. ......................... 604/294; 604/289; 604/290; 604/295
(58) Field of Search .............................. 604/8, 289, 290, 604/294, 1, 2

(56) References Cited

U.S. PATENT DOCUMENTS

| 4,540,408 | * | 9/1985 | Llyod | 604/294 |
| 4,838,851 | * | 6/1989 | Shabo | 604/1 |
| 4,883,454 | * | 11/1989 | Hamburg | 604/1 |
| 5,314,419 | * | 5/1994 | Pelling | 604/294 |
| 5,599,330 | * | 2/1997 | Rainin | 604/317 |
| 5,947,986 | * | 9/1999 | Lewis | 606/161 |

* cited by examiner

Primary Examiner—Kim M. Lewis
(74) Attorney, Agent, or Firm—John R. Benefiel

(57) ABSTRACT

A device and method of presenting an accurately controlled small volume of a Mitomycin solution to human eye tissues lining a conjunctival space created during surgery performed to correct glaucoma, using an absorbent pad mounted on one end of an elongated holder enabling insertion into the space. The pad is capable of retaining the Mitomycin solution after first being saturated with the Mitomycin solution prior to insertion and only very slowly releasing a consistently predictable small volume of solution directly onto the surrounding eye tissues. The holder has a portion to which the absorbent pad is attached, which is curved into conformity with the eyeball curvature to achieve better tissue contact. A handle allows insertion and removal from the space.

12 Claims, 2 Drawing Sheets

APPLICATOR AND METHOD FOR DELIVERY OF MITOMYCIN TO EYE TISSUES DURING GLAUCOMA FILTERING SURGERY

BACKGROUND OF THE INVENTION

The present invention pertains to an applicator for delivery of the proper dosage of Mitomycin C to eye tissues with a subconjunctival space created during glaucoma filtering surgery. Mitomycin C is an anti-neoplastic drug which also has a potent anti-scarring property that is highly desirable for glaucoma surgery. For the surgery to be successful, the surgically created subconjunctival space should remain open, so that an aqueous eye fluid called aqueous humor can continuously drain out through a surgically created opening through the eyeball wall. However, there is a tendency for the body to heal any wound by scar tissue formation at the wound, and this will gradually close the subconjunctival space. When the space becomes totally blocked, the eye fluid can not drain out, and the surgical correction fails. Mitomycin is used as an antimetabolite to prevent this scarring and closure of the drainage opening.

A brief description of the anatomy of the eye is in order, here made with reference to FIG. 1. The cornea 2 is the transparent front part of the eye which continues in to the white wall of the eye, the sclera 4. The colored part of the eye is the iris 6. The space between the cornea 2 and the iris 6, the anterior chamber 16, is filled with aqueous fluid. The much smaller space posterior to the iris is the posterior chamber 14. The root of the iris is attached to the ciliary body 10, which has many finger-like projections centrally, called the ciliary processes 12. The ciliary processes 12 secrete the aqueous fluid, and also project cobweb filaments to anchor the lens 24 in place. The cornea 2 and iris 6 converge to form the filtration angle wherein multi-layer sieve-like filters are located, referred to as trabecular meshworks 20.

There are pathways within the eye for aqueous humor circulation. With reference to FIG. 2, the ciliary processes 12 continuously secrete the aqueous humor, which keeps the eyeball distended and round, like air in a tire. The aqueous humor flows out to posterior chamber 14; then passes through the pupil 18 to the anterior chamber 16, thence to the trabecular meshworks 20 and into the Schlemm canal 22, and eventually out through outflow channels to the vein and systemic circulation. The amount of fluid introduced into the eye should equal the amount of fluid drained out. If the aqueous fluid leaving the eye is less than that introduced, the retained fluid will gradually build up pressure in the eye, similar to the effect of pumping more air into a tire to create a higher tire pressure. High eye pressure causes progressive nerve damage, and if not treated, eventual blindness. Medical treatment consists of using eye drops to lower the eye pressure. When medical therapy fails to lower the pressure, surgery is indicated.

In glaucoma there is too much aqueous fluid retained in the eye due to blockage in the filters and flow out vessels of the eye, causing elevated pressure.

Referring to FIG. 4, glaucoma corrective surgery involves forming an opening at the limbus 32 (cornea scleral junction) under a conjunctival flap, so that the fluid can continuously drain out to a subconjunctival space 28 formed by the surgery, and be absorbed into systemic circulation. The success of the surgery depends greatly on keeping this subconjunctival space open.

In recent years, more and more glaucoma surgeries are being performed with the help of anti-scarring drugs, notably the anti-metabolite Mitomycin C. The conventional method is to soak the operative area with Mitomycin solution using a completely saturated piece of sponge held in the space for few minutes. The operative area is then copiously rinsed with a saline solution to remove excess Mitomycin. This method of application has many inherent disadvantages. Firstly, the amount of the drug applied and absorbed by the tissues is excessive and uncertain as the volume of fluid flowing out from the easily compressed sponge is usually excessive and is not readily controlled or predicted. This procedure is thus mostly a matter of guesswork.

Secondly, there is a lack of consistency. Too little drug absorbed by the tissues will cause early surgical failure, and too much delivered will cause many serious complications due to the toxicity of the drug.

Thirdly, it is difficult to accurately apply the drug to the areas of the surrounding tissues which need to be treated.

Thus, the results are erratic and unpredictable.

If the subconjunctival space becomes blocked by scarring, which is the body's natural process of healing, the fluid can not drain out, and the surgery fails to correct the problem.

The object of the deliver invention is to provide an applicator which can present the proper dosage of an anti-scarring drug, i.e., Mitomycin C, for absorption by the tissues at the proper locations, with great consistency, to thus improve the rate of success for this type of surgery.

SUMMARY OF THE INVENTION

This and other objects of the present invention which will become apparent upon a reading of the following specification and claims are achieved by the use of an applicator device which includes an absorbent pad which retains a drug solution into which it has been dipped while delivery a controlled small volume of Mitomycin solution to the adjacent eye tissues in those precise areas that need to be treated, so that a proper dosage for absorption is delivered to these tissues. The pad may be formed of a rectangular piece of super absorbent fine fiber felt pad, attached to one end of an elongated support strip, preferably of brass. A high quality virgin paper is wrapped around both the pad and the one end of the support strip. The pad is not as easily compressed as a sponge material and allows only a very slow seepage of solution when in position, such that only a mere wetting of the tissues results.

The distal end of the strip serving as a handle has silicone rubber discs attached to improve the ability to reliably grasp and hold the device as with forceps.

The applicator device comprises three main parts, a handle, an off set, and a main body. The main body with the pad attached is the main functional part. The pad retains the drug solution and slowly releases only the correct volume of solution to the tissues of the eye lining the conjunctival space.

During surgery, the applicator is dipped into a medicine glass containing the Mitomycin solution to saturate the pad. The applicator is then picked up by its handle using forceps. The main body portion with the pad attached is then inserted under the conjunctival flap for a predetermined period, i.e., three minutes, that is sufficient time for the applicator to release only that volume of the solution necessary for a proper dosage to be delivered and absorbed by the tissues lining the subconjunctival space. As mentioned earlier, Mitomycin is used to prevent scarring and obliteration of this subconjunctival space into which the eye aqueous drained. The goal is to keep this space open so that the aqueous fluid can drain into it and eventually result in its absorption into the systemic circulation.

The applicator of the delivers invention accurately presents the proper amount of the drug only to those tissue surfaces to be treated, to cause the proper dosage to be absorbed by the tissues of the conjunctival space with great consistency. No post application irrigation is required. This is in sharp contrast to the conventional method of completely soaking the operative field, i.e., the subconjunctival space, with an uncontrolled excessive amount of Mitomycin solution, followed with copious irrigation to remove excess Mitomycin.

DESCRIPTION OF THE DRAWINGS FIGURES

DETAILED DESCRIPTION

In the following detailed description, certain specific terminology will be utilized for the sake of clarity and a particular embodiment described in accordance with the requirements of USC 112, but it is to be understood that the same is not intended to be limiting and should not be so construed inasmuch as the invention is capable of taking many forms and variations within the scope of the appended claims. The measurements and angles given are only the averages for a typical instrument according to the present invention.

Figure 6A:
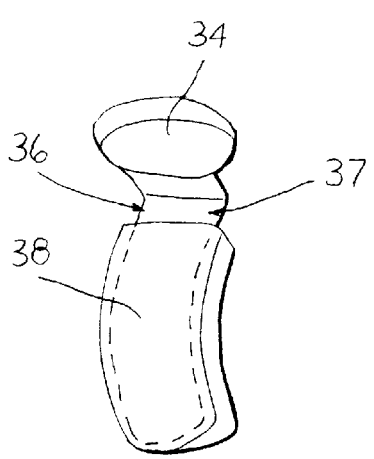
FIG. 6A is a top view of the applicator showing its main parts.
Figure 6B:
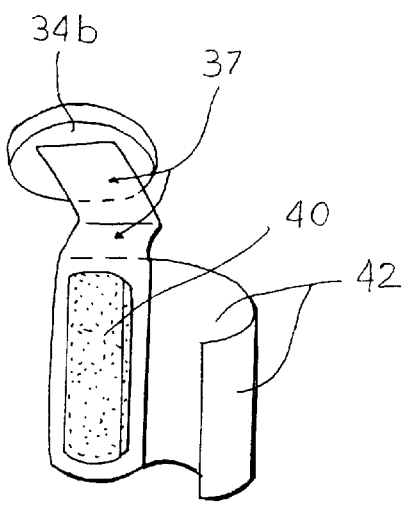
FIG. 6B is a partially exploded top view showing the components of the applicator.
Figure 7A:
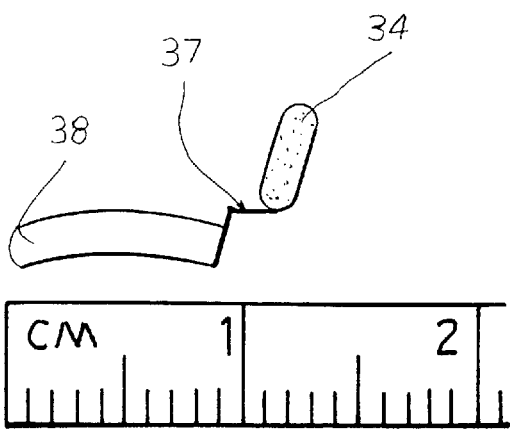
FIG. 7A is a side view of the applicator with a reference scale.
Figure 7B:
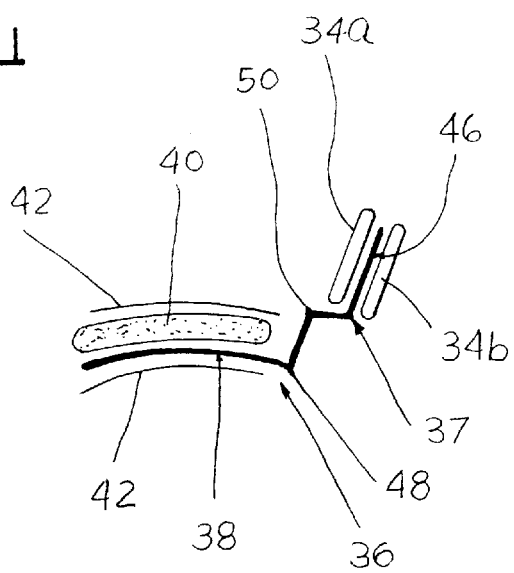
FIG. 7B is a partially exploded side view showing the main components and structure of the applicator.

Referring to the drawings and particularly FIGS. 6A, B and 7A, B, the applicator has four components, an elongated support strip 36, preferably made of brass; an absorbent pad 40; a paper shell 42; and, a pair of silicone rubber discs 34A, 34B covering the handle 46 to form a grip 34. The elongated strip 36 supports the other components, and has a thickness of about 0.12 mm to be somewhat flexible but stiff enough to hold its shape during normal handling. The strip 36 has a width of about 4 mm. The strip 36 includes a main body section 38, 9 mm long, to which the pad 40 is attached with a suitable adhesive. The side view of FIG. 7A reveals that the body section 38 has a gentle curve, with radius of curvature of about 14 mm, which approximately conforms to the average curvature of the human eyeball. The strip 36 also has an outer end 37, which has three angled sections, an upward right angle 48, extending 2 mm, a horizontal right angle section 50, extending 2 mm, and a 100 degree upward angulation 46, acting as the handle, 5 mm long. The right angle sections 48, 50, provide an offset of the handle 46 from the main body 38.

The pad 40 is rectangular strip, 3.5 mm×8 mm, and is made of Du Pont super absorbent polyester fine fiber felt 1.5 mm thick. The felt pad 40 is glued onto the main body 38 of the strip 36. It serves as the main drug delivering component. This type of fiber felt is chosen because of its good consistency only releasing a controlled secretion of Mitomycin solution onto the operative tissue area in contact with the pad. The paper shell 42 is made of a piece of high quality virgin paper, 9 mm×18 mm, and wraps the felt pad 40 onto the strip 36. The paper shell 42 is also absorbent to enhance the desired drug presenting capability of the pad 40.

The handle 46 has a pair of silicone rubber discs 34a, b, 5 mm in diameter attached thereto.

Figure 1:
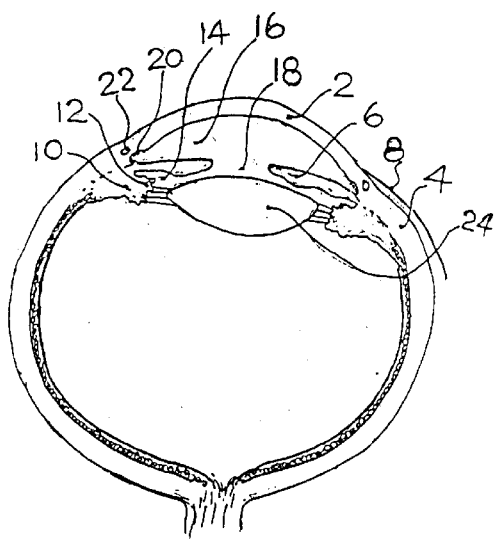
FIG. 1 is a sectional view of an eye showing the important parts involved in glaucoma surgery.
Figure 2:
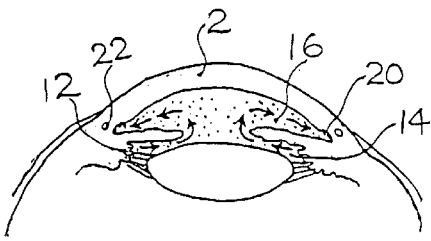
FIG. 2 is a sectional view of the angle structures of the eye showing the pathway of the aqueous fluid circulation in the eye.
Figure 3:
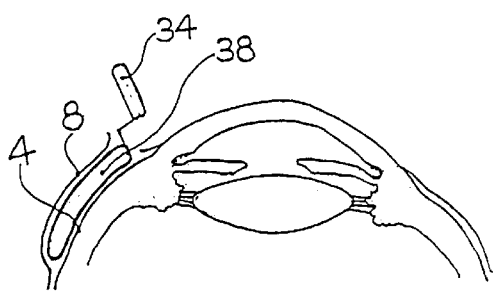
FIG. 3 is a sectional view of the anterior segment of the eye showing the position of the applicator during glaucoma surgery.
Figure 4:
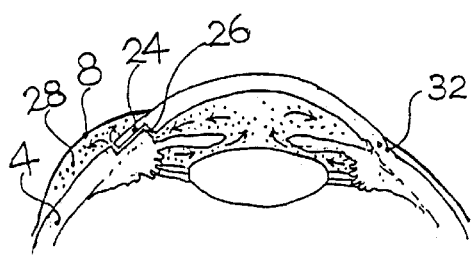
FIG. 4 is a sectional view of the anterior segment of the eye showing a successful glaucoma filtering surgery in which aqueous fluid is draining continuously into the subconjunctival space.
Figure 5:
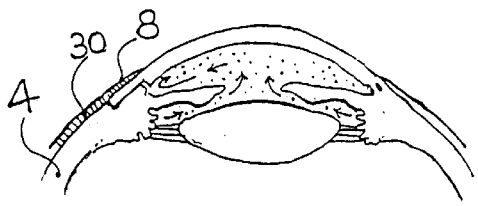
FIG. 5 is a sectional view of the anterior segment of the eye showing a failed glaucoma surgery in which the subconjunctival space is obliterated due to scarring.

During surgery, the applicator is deposited into a small jar containing the Mitomycin solution. After absorbing the solution for few minutes, the applicator is picked up by its handle with forceps and the end with the pad 40 attached is inserted under the conjunctival flap (FIG. 3). The pad 40 is allowed to remain there for a predetermined time interval, i.e., for about three minutes. During this time, an accurately predictable volume of Mitomycin solution slowly seeps out from the pad 40 to be delivered to the contacted tissues, and is then absorbed by the surrounding subconjunctival and episcleral tissues. This anti-scarring drug prevents the conjunctiva from sticking together with sclera, consequently keeping the subconjunctival space open.

Since the applicator creates a controlled slow release of the proper amount of Mitomycin solution to the adjacent tissues, no post application fluid irrigation of the treated area is required. This is a great advantage over the conventional method of flooding the operative field with an excessive volume of the solution followed by copious irrigation to wash away the excess drug. The present invention accurately delivers the proper dose of the drug only to the appropriate eye tissue areas with great consistency, thus significantly improving the chances of success for the glaucoma surgery.

I claim:

1. A method of applying a dosage of an antimetabolite fluid to tissues forming the conjunctival space of in the human eye of a patient, comprising the steps of:

providing an applicator comprising an elongate support, said elongate support being of sufficient stiffness to maintain its form during handling, said elongated support having a body portion having a first end on which an absorbent pad is secured and a second end defining a handle portion, said handle portion offset from said main body portion;

saturating said absorbent pad with an antimetabolite, said pad not being readily compressible so as to retain said fluid and only slowly secrete the same at a consistently predictable low rate when said pad is inserted into the conjunctival space of the eye;

inserting said pad into the conjunctival space so as to place the pad in contact with eye tissue lining the conjunctival space while holding said handle portion of said elongated support;

leaving said pad therein for a sufficient predetermined period of time to deliver an effective volume of antimetabolite fluid by secreting said antimetabolite fluid from said pad;

withdrawing said elongate support to remove said pad from the conjunctival space after the elapse of said sufficient predetermined period of time to deliver the effective volume of the fluid from said pad to cause absorption of a proper dose of the fluid to surrounding eye tissues.

2. The method according to claim 1 further including the step of constructing said pad from a strip of felt.

3. The method according to claim 2 wherein said absorbent pad is constructed from fine fiber polyester super absorbent felt.

4. The method according to claim 1 further including the step of forming said elongated strip from a brass strip.

5. The method according to claim 1 further including the step of covering said handle.

6. The method according to claim 1 wherein said handle portion is offset from said main body portion at an obtuse angle.

7. The method according to claim 1 further including the step of forming said pad to be approximately 8 mm long.

8. The method according to claim 1 further including the step of forming at said body portion of said elongated support to have a curved shape in approximate conformity to the curvature of the human eyeball shape prior to insertion of said body portion into the conjunctival space.

9. The method according to claim 8 further including the step of wrapping said pad in paper prior to saturating said pad with said antimetabolite fluid.

10. The method according to claim 9 further including the step of forming said handle portion with an offset between said body portion and said handle portion.

11. The method according to claim 10 further including the step of angling said handle portion from said offset.

12. The method according to claim 1 wherein a Mitomycin C solution is used as said antimetabolite fluid.

* * * * *